(12) United States Patent
Orringer et al.

(10) Patent No.: US 10,016,122 B2
(45) Date of Patent: *Jul. 10, 2018

(54) SURGICAL HEADLIGHT SYSTEMS AND METHODS FOR USE

(71) Applicant: Jay S. Orringer, M.D., A Professional Corporation, Beverly Hills, CA (US)

(72) Inventors: Jay S. Orringer, Encino, CA (US); JoLynne V. Orringer, Encino, CA (US); Jordan H. Orringer, Encino, CA (US); Thomas V. Root, Beverly, MA (US); Michael A. Cook, Marblehead, MA (US)

(73) Assignee: Jay S. Orringer, M.D., A Professional Corporation, Beverly Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/635,915

(22) Filed: Jun. 28, 2017

(65) Prior Publication Data
US 2017/0303776 A1    Oct. 26, 2017

Related U.S. Application Data

(63) Continuation of application No. 15/421,977, filed on Feb. 1, 2017, now Pat. No. 9,717,401.
(Continued)

(51) Int. Cl.
*A61B 90/30* (2016.01)
*A61B 1/06* (2006.01)
(Continued)

(52) U.S. Cl.
CPC ............ *A61B 1/0692* (2013.01); *A61B 90/30* (2016.02); *A61B 90/35* (2016.02); *F21L 4/00* (2013.01);
(Continued)

(58) Field of Classification Search
CPC .......... A42B 1/244; A42B 1/242; A61B 1/002; A61B 1/0692; A61B 90/30; A61B 90/36;
(Continued)

(56) References Cited

U.S. PATENT DOCUMENTS 1,688,113 A    10/1928   Bornkessel
3,830,230 A    8/1974    Chester
(Continued)

OTHER PUBLICATIONS

PCT International Search Report and Written Opinion in PCT International Application No. PCT/US2017/016052 dated Apr. 20, 2017.

*Primary Examiner* — Hargobind S Sawhney
(74) *Attorney, Agent, or Firm* — Greenberg Traurig, LLP; David J. Dykeman

(57) ABSTRACT

A surgical headlight system includes an adjustable headband, a light assembly mounted to the headband, a motor assembly mounted to the headband and the light assembly, and electronic controller having a wireless transceiver therein, a power control circuit for varying electrical power delivered to a light source of the light assembly, a power source in electrical communication with the light assembly, the motor assembly, and the wireless transceiver, and a sterilizable wireless controller configured to transmit instructions to the wireless transceiver, the instructions causing the electronic controller to one or more of actuate at least one motor of the motor assembly to alter an orientation of the light assembly, adjust a diameter of an aperture of the light assembly, adjust a spacing between one or more condensing lenses and an objective lens, or operate the power control circuit to increase or decrease electrical power delivered to the light source.

20 Claims, 5 Drawing Sheets

Related U.S. Application Data

(60) Provisional application No. 62/289,892, filed on Feb. 1, 2016.

(51) Int. Cl.

| | | |
|---|---|---|
| *F21L 4/00* | (2006.01) | |
| *F21V 21/14* | (2006.01) | |
| *F21V 21/15* | (2006.01) | |
| *F21V 33/00* | (2006.01) | |
| *H05B 37/02* | (2006.01) | |
| *F21V 5/04* | (2006.01) | |
| *F21V 23/00* | (2015.01) | |
| *A61B 90/35* | (2016.01) | |
| *F21W 131/205* | (2006.01) | |
| *A61B 90/50* | (2016.01) | |
| *F21Y 115/10* | (2016.01) | |

(52) U.S. Cl.
CPC .............. *F21V 5/04* (2013.01); *F21V 21/145* (2013.01); *F21V 21/15* (2013.01); *F21V 23/001* (2013.01); *F21V 33/0068* (2013.01); *H05B 37/0272* (2013.01); *A61B 2090/502* (2016.02); *F21W 2131/205* (2013.01); *F21Y 2115/10* (2016.08)

(58) Field of Classification Search
CPC ......... A61B 90/50; A61B 1/06; A61B 1/0607; A61B 1/0684; A61B 1/07; F21V 21/084; F21V 21/15; F21V 21/22; F21V 21/28; F21V 21/30; F21V 21/26; F21V 33/0068; F21W 2131/20; F21W 2131/202; F21Y 2113/13; Y10S 362/804; F21L 4/00; G02B 7/002

See application file for complete search history.

(56) References Cited

U.S. PATENT DOCUMENTS

| | | | | |
|---|---|---|---|---|
| 4,616,257 | A | * | 10/1986 | Kloots ................... F16M 13/04 348/370 |
| 5,430,620 | A | * | 7/1995 | Li ........................... F21L 14/00 362/105 |
| 5,709,459 | A | * | 1/1998 | Gourgouliatos ........ F21L 14/00 362/105 |
| 5,769,523 | A | * | 6/1998 | Feinbloom .............. F21L 14/00 362/105 |
| D406,371 | S | | 3/1999 | Van Der Bel |
| 6,224,227 | B1 | | 5/2001 | Klootz |
| 6,955,444 | B2 | | 10/2005 | Gupta |
| 7,041,054 | B2 | | 5/2006 | Klootz |
| 7,134,763 | B2 | | 11/2006 | Klootz |
| 7,314,300 | B1 | | 1/2008 | Dorr et al. |
| 8,348,448 | B2 | | 1/2013 | Orozco et al. |
| 8,789,962 | B2 | | 7/2014 | Crowder |
| 9,326,827 | B2 | | 5/2016 | Estwick et al. |
| 9,717,401 | B1 | | 8/2017 | Orringer et al. |
| 2006/0285315 | A1 | | 12/2006 | Tufenkjian |
| 2013/0322053 | A1 | | 12/2013 | Kim et al. |
| 2014/0293589 | A1 | | 10/2014 | Estwick et al. |
| 2014/0336472 | A1 | | 11/2014 | Ferguson |

* cited by examiner

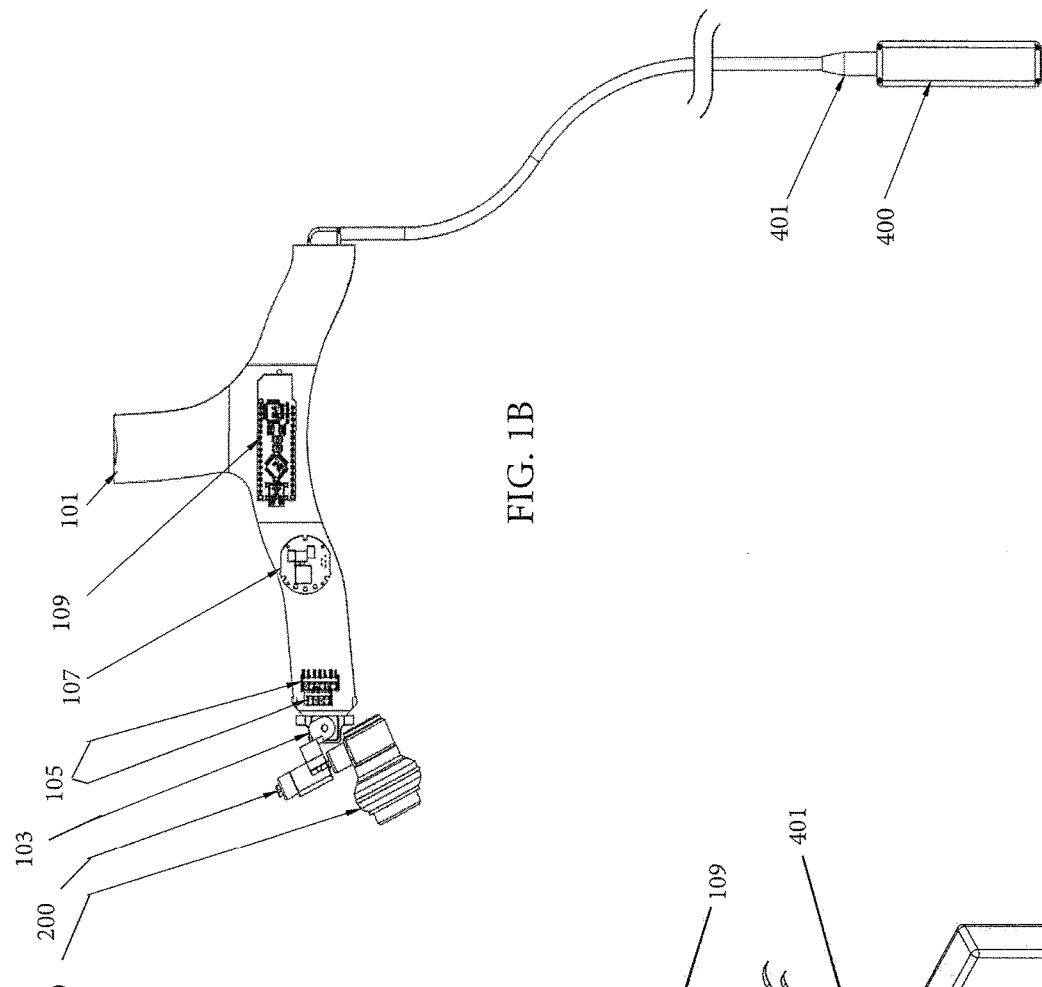
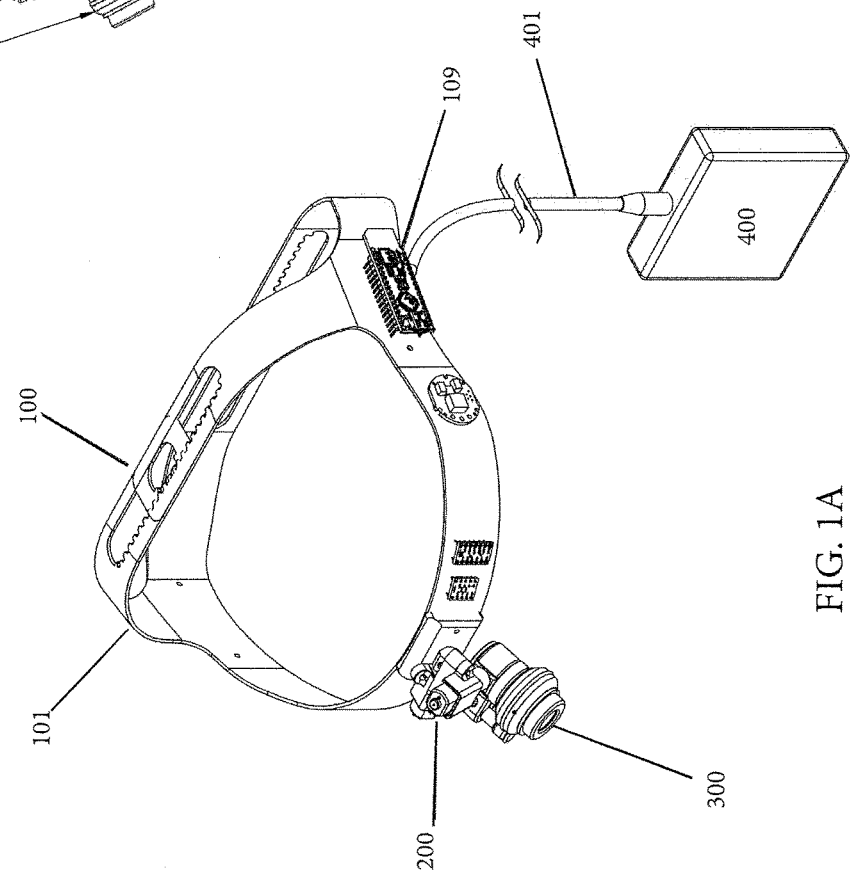
FIG. 1B
FIG. 1A

SURGICAL HEADLIGHT SYSTEMS AND METHODS FOR USE

CROSS-REFERENCE TO RELATED APPLICATIONS

This application is a continuation of U.S. application Ser. No. 15/421,977, filed Feb. 1, 2017, which claims priority to and the benefit of U.S. Provisional Application No. 62/289,892, filed Feb. 1, 2016, the contents of each of which are incorporated herein by reference in their entirety.

TECHNICAL FIELD

Example embodiments relate generally to headlights, more particularly, to wireless surgical headlights.

BACKGROUND

Conventional surgical headlights are not sterile. Conventionally, the illumination beam is directed towards and manipulated within the surgical field through the motion of the wearer's head. If this direction is uncomfortable for the wearer, the wearer must either break the sterilization by physically redirecting the beam or else having an assistant adjust the headlight.

SUMMARY

In some embodiments a surgical headlight system is provided. The surgical headlight system includes an adjustable headband for a head of a user. The surgical headlight system also includes a light assembly mounted to the headband. The light assembly includes a light source having variable light output. The light assembly also includes an optical assembly including an adjustable diameter aperture in optical communication with the light source. The surgical headlight system also includes a motor assembly mounted to the headband and the light assembly. The motor assembly includes a first motor configured to alter an orientation of the light assembly relative to a horizontal plane. The motor assembly also includes a second motor configured to alter an orientation of the light assembly relative to a vertical plane. The motor assembly also includes a third motor configured to adjust the diameter of the aperture. The surgical headlight system also includes an electronic controller mounted to the headband. The electronic controller includes a wireless transceiver. The electronic controller also includes a power control circuit for varying electrical power delivered to the light source. The surgical headlight system also includes a power source in electrical communication with the light source, the motor assembly, and the wireless transceiver. The surgical headlight system also includes a sterilizable wireless controller configured to transmit instructions to the wireless transceiver, the instructions causing the electronic controller to one or more of actuate at least one of the first motor or second motor of the motor assembly to alter the orientation of the light assembly relative to at least one of the vertical plane or the horizontal plane, actuate the third motor of the motor assembly to adjust the diameter of the aperture, or operate the power control circuit to increase or decrease electrical power delivered to the light source to vary a light output of the light source, or any combinations thereof.

In some embodiments the wireless controller is sterilized by autoclave. In some embodiments control of the light within the sterile field is maintained by insertion of the wireless controller within a sterile, radiotransparent receptacle. In some embodiments the wireless controller includes a controller power source. In some embodiments the surgical headlight system includes a belt for a waist of a user, the power source mounted to the belt. In some embodiments the wireless controller includes at least one joystick or linear potentiometer for receiving input from the user. In some embodiments the light source is a light-emitting diode (LED). In some embodiments the light assembly further comprises a fiber optic cable in optical communication with the optical assembly. In some embodiments the light assembly further comprises one or more condensing lenses and an objective lens in optical communication with the light source.

In some embodiments a surgical headlight system is provided. The surgical headlight system includes an adjustable headband for a head of a user. The surgical headlight system also includes a light assembly mounted to the headband. The light assembly includes a light source having variable light output. The light assembly also includes an optical assembly including an adjustable diameter aperture in optical communication with the light source. The surgical headlight system also includes a motor assembly mounted to the headband and the light assembly. The motor assembly includes a first motor configured to alter an orientation of the light assembly relative to a horizontal plane. The motor assembly also includes a second motor configured to alter an orientation of the light assembly relative to a vertical plane. The motor assembly also includes a third motor configured to adjust a spacing between the one or more condensing lenses and objective lens. The surgical headlight system also includes an electronic controller mounted to the headband. The electronic controller includes a wireless transceiver. The electronic controller also includes a power control circuit for varying electrical power delivered to the light source. The surgical headlight system also includes a power source in electrical communication with the light source, the motor assembly, and the wireless transceiver. The surgical headlight system also includes a sterilizable wireless controller configured to transmit instructions to the wireless transceiver, the instructions causing the electronic controller to one or more of actuate at least one of the first motor or second motor of the motor assembly to alter the orientation of the light assembly relative to at least one of the vertical or horizontal planes, actuate the third motor of the motor assembly to adjust the spacing between the one or more condensing lenses and objective lens, or operate the power control circuit to increase or decrease electrical power delivered to the light source to vary a light output of the light source, or any combinations thereof.

In some embodiments the wireless controller is sterilized by autoclave. In some embodiments control of the light within the sterile field is maintained by insertion of the wireless controller within a sterile, radiotransparent receptacle. In some embodiments the wireless controller includes a controller power source. In some embodiments the surgical headlight system includes a belt for a waist of a user, the power source mounted to the belt. In some embodiments the wireless controller includes at least one joystick or linear potentiometer for receiving input from the user. In some embodiments the light source is a light-emitting diode (LED). In some embodiments the light assembly further comprises a fiber optic cable in optical communication with the optical assembly. In some embodiments the light assembly further comprises an adjustable diameter aperture in optical communication with the light source.

In some embodiments a method for operating a surgical headlight is provided. The method includes illuminating a surgical site with a beam of light emitted from a light assembly mounted to an adjustable headband of a surgical headlight worn by a user. The method also includes transmitting, in response to receiving a user input at a sterilizable wireless controller, instructions from the wireless controller, via a wireless transceiver mounted to the headband, to an electronic controller mounted to the headband. The method also includes, in response to receiving the instructions at the electronic controller, one or more of actuating at least one of a first motor or a second motor of a motor assembly mounted to the headband and operatively connected to the light assembly, to alter the orientation of the light assembly relative to at least one of a vertical plane or a horizontal planes, actuating a third motor of the motor assembly to adjust at least one of a diameter of an aperture of the light assembly or a spacing between one or more condensing lenses and an objective lens of the light assembly, or operating a power control circuit mounted to the headband to increase or decrease electrical power delivered to a light source of the light assembly to vary a light output of the light source.

In some embodiments, the method also includes providing the user input to the wireless controller from within a surgical sterile field.

BRIEF DESCRIPTION OF THE DRAWINGS

Illustrative, non-limiting example embodiments will be more clearly understood from the following detailed description taken in conjunction with the accompanying drawings.

FIG. 1A, FIG. 1B, and FIG. 1C are perspective, side, and exploded assembly views of a surgical headlight in accordance with various embodiments.

DETAILED DESCRIPTION OF THE EMBODIMENTS

Figure 1C:
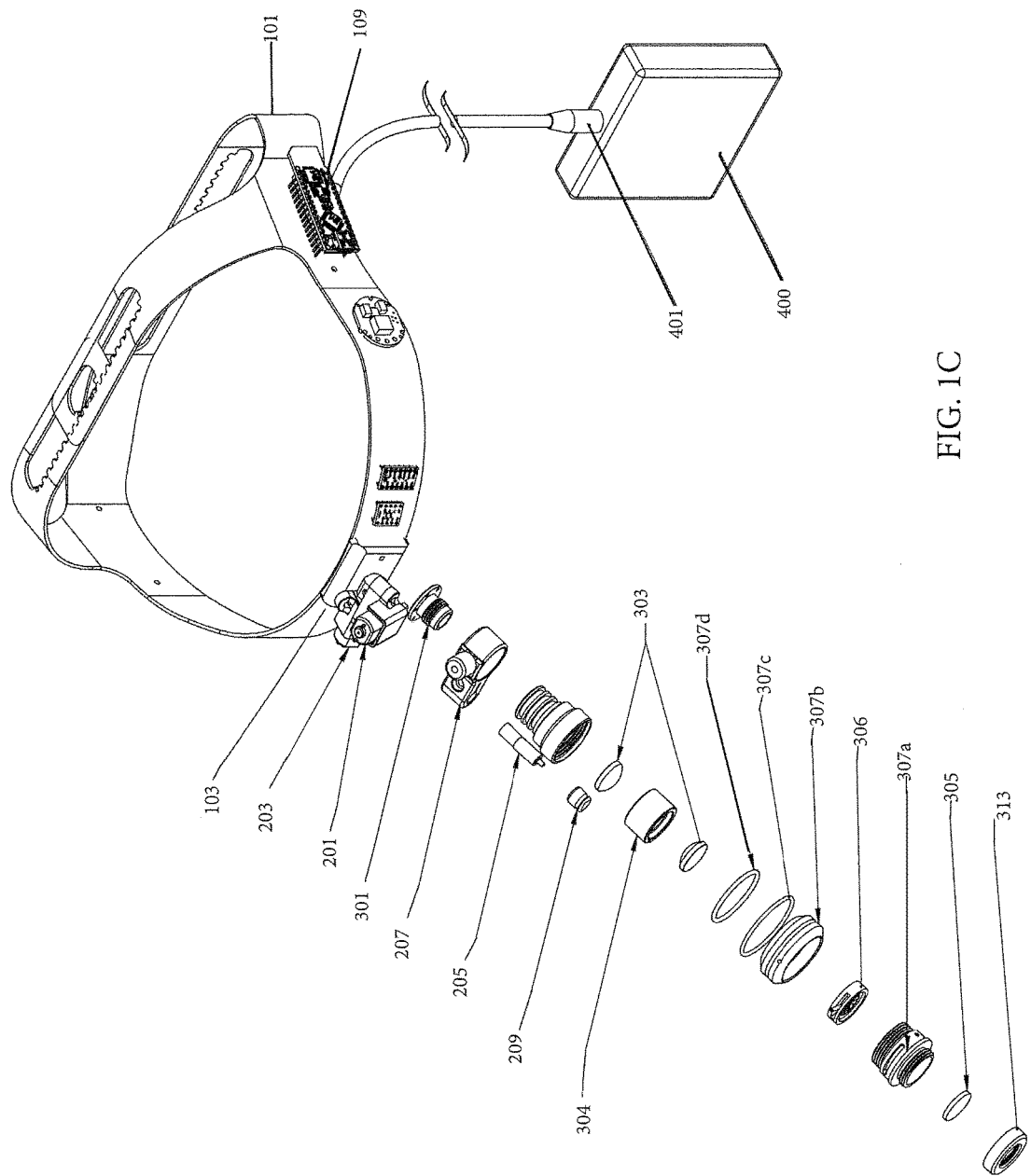

Various exemplary embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this disclosure will be thorough and complete, and will fully convey the scope of the present inventive concept to those skilled in the art. In the drawings, the sizes and relative sizes of layers and regions may be exaggerated for clarity. Like numerals refer to like elements throughout.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Embodiments of the present disclosure generally apply to wireless surgical headlights. The various embodiments of the present disclosure can, be used, for example, to provide steering and/or manipulation of a surgical headlight from within a sterile field of an operating room during a surgical procedure by a user or by an assistant.

FIG. 1A, FIG. 1B, and FIG. 1C illustrate a surgical headlight 100 in accordance with various embodiments of the present disclosure. The surgical headlight 100 can include an adjustable headband 101 for fitting to a head of a user. The surgical headlight 100 can also include a mounting assembly 103 for operative engagement with a motor assembly 200 configured to adjust an orientation and an aperture diameter of a light assembly 300. The surgical headlight 100 can also include a light source power control circuit 107 for increasing or decreasing electrical power delivered to a light source 301 of the light assembly 300 from a power source 400 in electrical communication (e.g., via a power cord 401) with the surgical headlight 100, thereby increasing or decreasing light output of the light source 301. The surgical headlight 100 can also include one or more motor control circuits 105 for controlling operation of the motors 201, 203, 205 of the motor assembly 200 and a processor 109 including a transceiver for communication with a wireless controller 500 (see FIG. 2A and FIG. 2B).

Figure 1E:
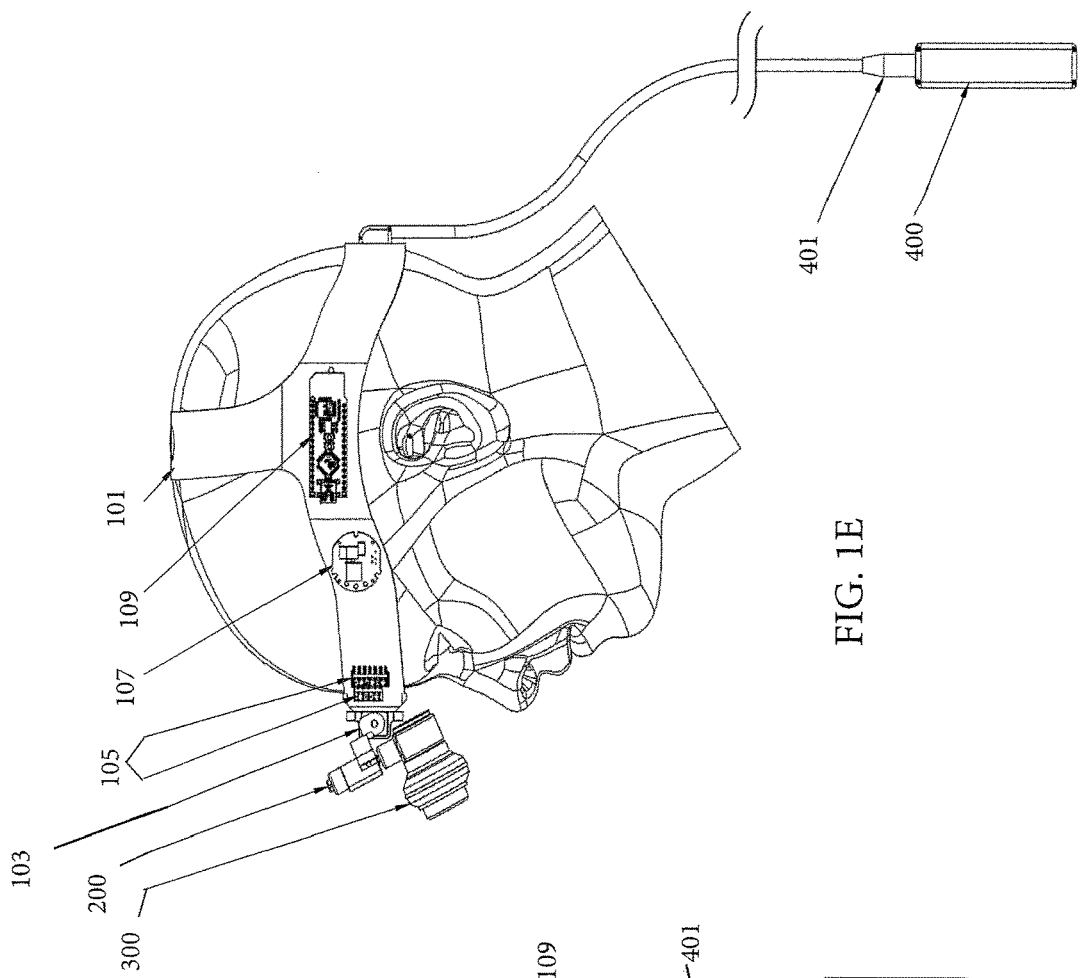
FIG. 1D and FIG. 1E are perspective and side views of the surgical headlight worn by a user in accordance with various embodiments.
Figure 1D:
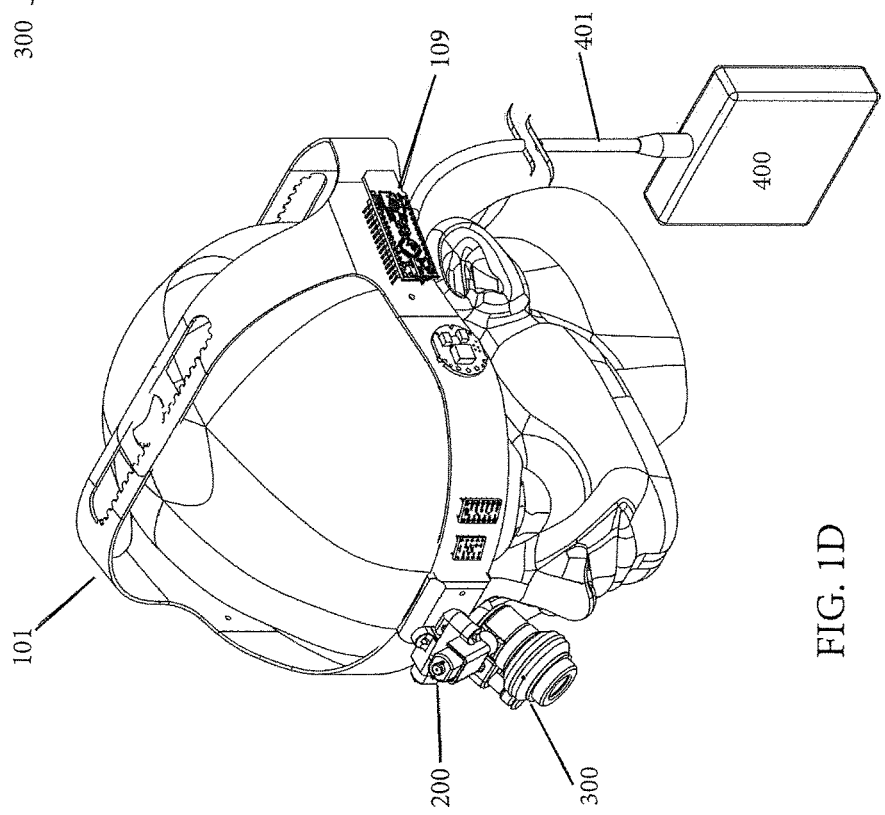

The headband 101, in accordance with various embodiments, can be constructed of any suitable material including, for example, plastics such as nylon 6, textiles such as medical grade elastic sweat bands, leather, polyamide film, or combinations thereof. In accordance with various embodiments, as shown in FIG. 1D and FIG. 1E, the headband 101 can be adjustable for providing a proper fit to a head of the user. Additionally, the headband 101, in accordance with various embodiments, can be soft enough to provide comfort to the user while providing sufficient strength and stiffness to retain and support the mounting assembly 103, motor assembly 200, light assembly 300, and any other components (e.g., circuits 105, 107, 109, power source 400, or power cord 401) of the surgical headlight 100. In some embodiments such as, for example, wherein the headband 101 is constructed of a polyamide film, the headband 101 can be implemented as a flexible circuit board. In such embodiments, one or more of the circuits and processors 105, 107, 109 can be integrally formed in the flexible circuit board of the headband 101. Additionally, in accordance with various embodiments, one or more ergonomic elements (not shown) such as pads, covers, molded elements, or cushions can be provided along an interior surface of the headband 101 or covering the headband 101 to provide additional comfort to the head of the user.

The mounting assembly 103, in accordance with various embodiments, can include one or more brackets, gimbals, ball and socket joints, or other structures suitable for retaining the motor assembly 200 and the light assembly 300 on the headband 101 while permitting rotation of the light assembly 300 by the motor assembly 200 relative to vertical and horizontal spatial planes within the user's field of view.

The motor control circuits 105 can be included in any suitable circuit or processor for controlling the one or more motors 201, 203, 205 of the motor assembly 200. For example, in accordance with various embodiments, the motor control circuits 105 can be included in one or more of a printed circuit board, a microprocessor, a microcontroller, a microprocessor, any other suitable electronic circuit, or combinations thereof.

The light source power control circuit 107 can be included in any suitable circuit or processor for varying electrical power delivered to the light source 301 of the light assembly 300. For example, in accordance with various embodiments, the light source power control circuit 107 can be included in one or more of a printed circuit board, a microprocessor, a microcontroller, any other suitable electronic circuit, or combinations thereof.

The processor 109, in accordance with various embodiments, can be included in one or more of a smartphone, a smart device, a tablet, a microprocessor, a microcontroller, a field programmable gate array (FPGA), or any other device suitable for incorporating a transceiver and for transmitting or receiving electronic data. In some embodiments, the processor 109 is configured to receive instructions for operation of the surgical headlight 100 from the controller processor 507 of the wireless controller 500. In some embodiments, the processor 109 is configured to transmit operational status data such as, for example, a position or orientation of the light assembly 300, a light output of the light source 301, a diameter of an aperture 306 of the light assembly 300, and/or a position of one or more lenses 303, 305 within the light assembly 300.

In some embodiments, one or more of the motor control circuits 105, light source power control circuit 107, and processor 109 and transceiver can be integrally formed within the headband 101 wherein, for example, the headband 101 is constructed of a flexible circuit board material such as polyamide film. In such embodiments, the motor driver circuits 105, the light source power control circuit 107, and the processor 109 and transceiver can be provided in a single integral configuration whereby all interconnections and wires between the components would be internal traces. In some embodiments, such a design would advantageously reduce size, weight, assembly labor, wires, and cost, while increasing reliability by decreasing the number of separate components. In such embodiments, a separate headband would be unnecessary because the integral headband-circuit would form the headband 101. In some embodiments, one or more ergonomic elements (not shown) such as pads, covers, molded elements, or cushions can be provided along an interior surface of the headband 101 or covering the headband 101 to provide additional comfort to the head of the user. Covers or covering material, in some embodiments, can be used to wrap around the headband 101 electronics and also provide removable ergonomic elements and removable padding. In some embodiments, the covering or padding can be removably attached by one or more of snaps, zippers, Velcro, laces, any other suitable mechanical fasteners, or combinations thereof.

The motor assembly 200, in accordance with various embodiments, can include first, second, and third motors 201, 203, 205, a motor mounting arm 207, and a drive wheel 209. The first motor 201, second motor 203, and third motor 205, in accordance with various embodiments, can each include one or more of a brushed permanent magnet DC motor, a brushless DC motor, a brushless AC motor, an AC induction motor, a gimbal servo, a brushless gimbal, or combinations thereof. It will be apparent in view of this disclosure that, in accordance with various embodiments, any number of motors can be used in accordance with various embodiments.

As shown in FIG. 1C, the first motor 201 can be configured to rotate the light assembly 300 left and right relative to a vertical plane within the user's field of view and the second motor 203 can be configured to rotate the light assembly 300 up and down relative to a horizontal plane within the user's field of view.

The third motor 205, in some embodiments, can be configured to adjust the diameter of the aperture 306 to control the amount of light. It will be apparent in view of this disclosure that any aperture structure configured for motorized operation can be used in connection with various embodiments. In particular, as shown in FIG. 1C, in some embodiments the third motor 205 can be mounted adjacent to the light assembly 300 in the motor mounting arm 207. In some embodiments, the third motor 205 can be configured to rotate drive wheel 209 of light assembly 300, which, in turn, can rotate an aperture control knob 307b by, for example, frictional engagement with a friction drive o-ring 307c extending around the aperture control knob 307b. The aperture control knob 307b, in turn, can rotate aperture housing 307a by, for example, frictional engagement with a knob friction o-ring 307d extending around the aperture housing 307a. The rotation of the aperture housing 307a, in turn, controls a diameter of an opening in the aperture 306 to control a diameter of a light beam emitted from the light assembly 300 of the surgical headlight 100.

The light assembly 300, in accordance with various embodiments, can include a light source 301 in optical alignment with the aperture 106 for emitting light therethrough. In some embodiments, the light assembly 300 can also include one or more lenses 303, 305. For example, as shown in FIG. 1C, the light assembly 300 includes first condensing lens and second condensing lens 303 and an objective lens 305 in optical communication with the light source 301 and the aperture 306 for focusing and shaping light energy emitted by the light source 301 to form a light beam (e.g., a variable width beam including beam angle and spot size) to be emitted by the light assembly. In some embodiments, spacing between the condensing lenses 303 and objective lenses 305 can be adjusted to control a shape and width of the light beam. It will be apparent in view of this disclosure that, although depicted in FIG. 1C as having both an aperture 306 and lenses 303, 305 for controlling beam shape and width, in some embodiments the light assembly 300 can include only lenses 303, 305 or, alternatively, only an aperture 306.

The light assembly 300, in some embodiments, can further include a lens mounting ring 304 for retaining the condensing lenses 303 in optical communication with the light source 301. In some embodiments, the lens mounting ring 304 can be retained within an outer lens housing 311 configured to engage at a first end with the motor assembly 200 and at a second end to the aperture housing 307a. The aperture housing 307a can be engaged, opposite the outer lens housing, with a lens retaining collar for retaining the objective lens 305 in optical alignment with the aperture 306, the condensing lenses 303, and the light source 301.

The light source can be any suitable light source including, for example, an incandescent bulb, a halogen bulb, a fiber optic cable, a light pipe, a light emitting diode (LED), a compact fluorescent bulb (CFL), any other suitable light emitting device, or combinations thereof.

The condensing lenses 303 and objective lens 305 can be constructed of any suitable material including polycarbonate, glass, polymers, plastics, polymethyl-methacrylate (PMMA), sapphire, or combinations thereof. Each of the condensing lenses 303 and objective lens 305 can be any suitable lens configuration known in the art. For example, configurations of the condensing lenses 303 and objective lens 305 can include one or more of biconvex, plano-convex, positive meniscus, negative meniscus, plano-concave, biconcave, photographic, doublet, triplet, achromatic, compound, Fresnel, or combinations thereof.

The power source 400, in accordance with various embodiments can include, for example, one or more batteries such as alkaline, nickel metal hydride (NiMH), nickel cadmium (NiCad), lithium ion (Li-ion), lithium polymer (Li-Po), primary batteries, secondary batteries, a battery pack, an AC power source, an AC/DC adapter, or combinations thereof. In some embodiments, the power source 400 can deliver power to the surgical headlight 100 via a power cord 401. For example, in FIG. 1A, FIG. 1B and FIG. 1C the power source 400 is depicted as a belt-mountable battery pack connected to the headlight 100 via power cord 401. However, it will be apparent in view of this disclosure that, in some embodiments, the power cord 401 can be an AC power cord or AC/DC adapter cord for being plugged into a conventional electrical outlet. It will be further apparent in view of this disclosure that, in some embodiments, the power source 400 can be mounted directly to the headband 101 or in any other suitable location for delivering power to the headlight 100.

It will be apparent in view of this disclosure that, in accordance with various embodiments, additional components can be added to the headlight 100. For example, in some embodiments, one or more image sensors, cameras, or video cameras can be mounted to the headlight 100 (e.g., on the headband 101 or the light assembly 200). In some embodiments, for example, a single video camera or image sensor can be mounted to the headlight 100 to provide first-person video of a surgical procedure. In some embodiments, for example, two video cameras or image sensors can be spaced apart along the headband 101 to provide three-dimensional imagery or video. In some embodiments, the one or more image sensors or video cameras can be fixed in relation to the user's field of view. In some embodiments, the one or more image sensors or video cameras can be steerable with, or independent of, the light assembly 200. In some embodiments, the recorded images or video can be stored in a memory of the headlight 100 or can be transmitted via the wireless transceiver or one or more wires to one or more external memory storage devices.

In some embodiments, the headlight 100 can further include one or more audio sensors. The one or more audio sensors can be used, for example, for receiving voice commands, recording the user's or a medical practitioner's verbal notes with respect to a medical or surgical procedure, recording audio to accompany a video recorded by one or more image or video sensors as discussed above, and/or for providing a "black box" type record of the procedure. In some embodiments, the recorded audio can be stored in a memory of the headlight 100 or can be transmitted via the wireless transceiver or one or more wires to one or more external memory storage devices.

Figure 2B:
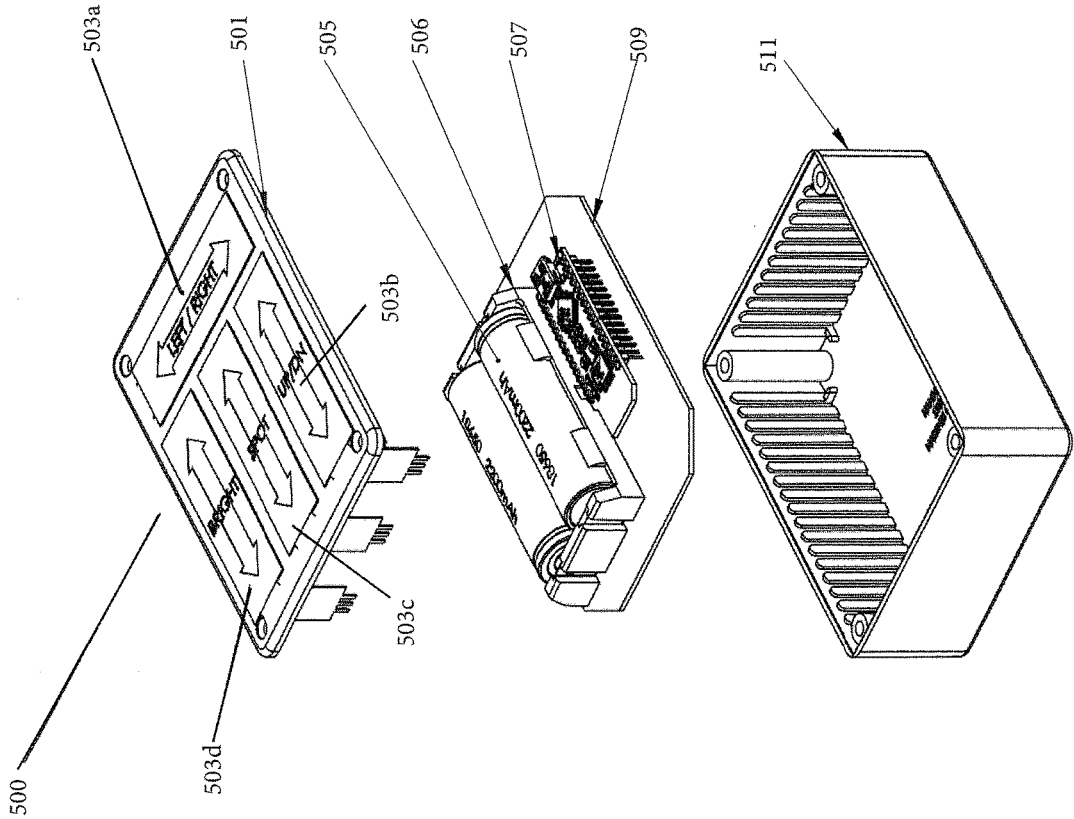
FIG. 2A and FIG. 2B are top and exploded assembly views of a wireless controller in accordance with various embodiments.
Figure 2A:
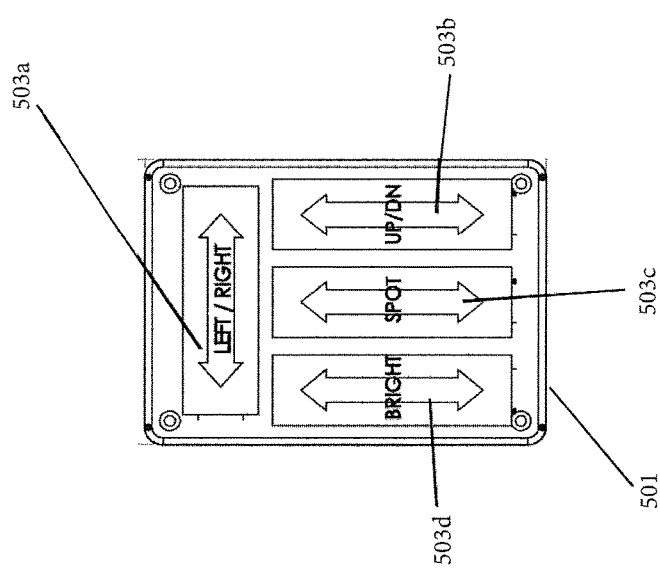

Referring now to FIG. 2A and FIG. 2B, the wireless controller 500, in some embodiments, includes a control surface 501 having a plurality of controls 503a, 503b, 503c, and 503d disposed thereon. The wireless controller can also include a case 511 and a substrate 509 positioned within the case 511. The substrate 509 (e.g., a polycarbonate board) includes one or more retention features 506 (e.g., a battery "sled" as shown) attached thereto and for holding or retaining a controller processor 507 and a controller power source 505. In some embodiments, additional circuitry may be incorporated into the wireless controller 500 so that, for example, a wall-plug transformer (not shown) may plug-in to the case 511 as a means for re-charging the internal batteries as needed. In some embodiments, an indicator or display can be provided to indicate operational status and/or remaining battery life to the user.

The controls 503a, 503b, 503c, and 503d of the control surface 501 can include one or more controls for operating the surgical headlight 100. For example, as shown in FIG. 2A and FIG. 2B, controls 503a, 503b, 503c, and 503d can include one or more of a left/right control 503a for instructing the motor assembly 200 to rotate the light assembly 300 left and right relative to a vertical plane within the user's field of view, an up/down control 503b for instructing the motor assembly 200 to rotate the light assembly 300 up and down relative to a horizontal plane within the user's field of view, a spot control 503c for instructing the motor assembly 200 to vary the aperture diameter to increase or decrease the size of the light beam, and a brightness control 503d for instructing the power control circuit 105 to vary the electrical power delivered to the light source 301 to increase or decrease light output (brightness) of the light source 301. Each of the controls 503a, 503b, 503c, and 503d can be constructed using any suitable control mechanism including, for example, one or more of a potentiometer, a joystick, a button, a slide switch, a touchscreen, a track pad, a track ball, any other suitable control mechanism, or combinations thereof.

The controller power source 505 can include one or more batteries such as alkaline, nickel metal hydride (NiMH), nickel cadmium (NiCad), lithium ion (Li-ion), lithium polymer (Li-Po), primary batteries, secondary batteries, or combinations thereof, a battery pack, an AC power source, an AC/DC adapter, or combinations thereof.

The controller processor 507, in accordance with various embodiments, can be, for example, one or more of a smartphone, a smart device, a tablet, a microprocessor, a microcontroller, a field programmable gate array (FPGA), or any other device suitable for incorporating a transceiver and for transmitting or receiving electronic data. In some embodiments, the controller processor 507 is configured to transmit instructions to the processor 109 for operation of the surgical headlight 100, wherein the instructions are received from the controls 503a-d of the wireless controller 500. In some embodiments, the controller processor 507 is configured to receive from the processor 109 operational status data such as, for example, a position or an orientation of the light assembly 300, a light output of the light source 301, an diameter of an aperture 306 of the light assembly 300, and/or a position of one or more lenses 303, 305 within the light assembly 300.

The processor 109 of the surgical headlight 100 and the controller processor 507 can, in accordance with various embodiments, communicate electronically via any suitable method including, for example, near field communication (NFC), Bluetooth®, wifi, cellular networks, any other suitable wireless communications, or combinations thereof.

In some embodiments, the substrate 509, controller power source 505, and controller processor can advantageously be contained within the case 511 of the wireless controller 500. In some embodiments the case 511, in combination with the control surface, can be one or more of rigid, padded, waterproof, insulated, chemically resistant, and/or provide shielding from electromagnetic radiation. In some embodiments, the case 511 may be made from any suitable material including, for example, Acrylonitrile butadiene styrene (ABS), polycarbonate (PC), polypropylene (PP), nylon, or combinations thereof. In some embodiments, the wireless controller 500 is sterilizable by, for example, chemical disinfection and/or autoclave to permit use of the wireless controller within a surgical sterile field. In such embodiments, the wireless controller 500 should preferably be constructed of an autoclavable material such as, for example, polycarbonate. In some embodiments, the wireless controller 500 can be operated from within a sterile covering such as, for example, a sterile bag, thereby permitting use of the non-sterile wireless controller within the surgical sterile field. Use of the wireless controller within the surgical sterile field advantageously obviates the need for a party outside the surgical field to manipulate the headlight and thus saves both time and ergonomic and mental fatigue on the surgeon/wearer.

Although the surgical headlight 100 is illustrated and described herein as receiving user input at the wireless controller 500 and transmitting instructions to the headlight 100 via a wireless communications link, the wireless controller 500 can be optional and any other suitable means of receiving user input to provide instructions for controlling, steering, or manipulating the surgical headlight 100 without breaking the surgical sterile field are contemplated.

For example, in some embodiments, one or more sensors (e.g., proximity sensors, hall effect sensors, motion sensors, image sensors, cameras, video cameras, or other suitable sensors) can be mounted to the headband and configured to detect a position of one or more facial features of the user's face or one or more targets (e.g., stickers with metallic dots) positioned on the user's face. In such embodiments, steering/manipulation of the motors, spot size, and brightness, can be controlled in response to the user flexing or otherwise moving facial muscles. For example, in some embodiments, the user, can perform movements such as raising or lowering the user's ears, clenching the user's jaw, or making exaggerated cheek movements. In some embodiments, codes such as a specified number (e.g., two) of jaw clenches can be used to turn on the headlight 100 and a different number of jaw clenches (e.g., three) cab be used to turn off the headlight 100. Other movements or codes can be used to perform other control tasks such as left/right movement, up/down movement, aperture control, beam shaping, or brightness control.

In some embodiments, one or more image sensors, video cameras, or motion sensors can be positioned on the headlight 100 to track the user's eyes. The eye tracking data can then be analyzed by, for example, the processor 109 to synchronize an orientation or movement of the light assembly 200 with the user's eye movement. In some embodiments the eye tracking data can further be configured to detect the user blinking, wherein a particular pattern of blinking (e.g., three rapid blinks) can be used to initiate eye tracking control, adjust brightness, shape or manipulate the light beam, or otherwise manipulate, control, or steer the headlight 100.

In some embodiments, one or more audio sensors can be provided and the processor 107 can include program instructions for recognizing voice commands of the user to provide manipulation, control, and/or steering of the headlight 100. Voice commands can include any suitable command such as, for example, "pan left three degrees, angle up two degrees" to move the light assembly 200 three degrees leftward and two degrees upward or "brightness six, spot nine" to set the brightness to a predetermined setting of six (e.g., correlating to 60% of maximum power delivered to the light source 201) and set a beam (spot) diameter to a predetermined setting of nine (e.g., correlating to 90% of maximum diameter).

Such alternative control methods can, in some embodiments, advantageously reduce the number of separate hardware components that the user requires to operate the headlight 100. Additionally, such alternative control methods can advantageously obviate the need for the user to operate the headlight 100 with the user's hands, permitting the user to, for example, manipulate the headlight 100 without withdrawing the user's hands from a patient-subject during a procedure. Furthermore, such alternative control methods can eliminate the need for a wireless communication link, thereby avoiding potential interference from other proximate wireless devices.

Figure 3:
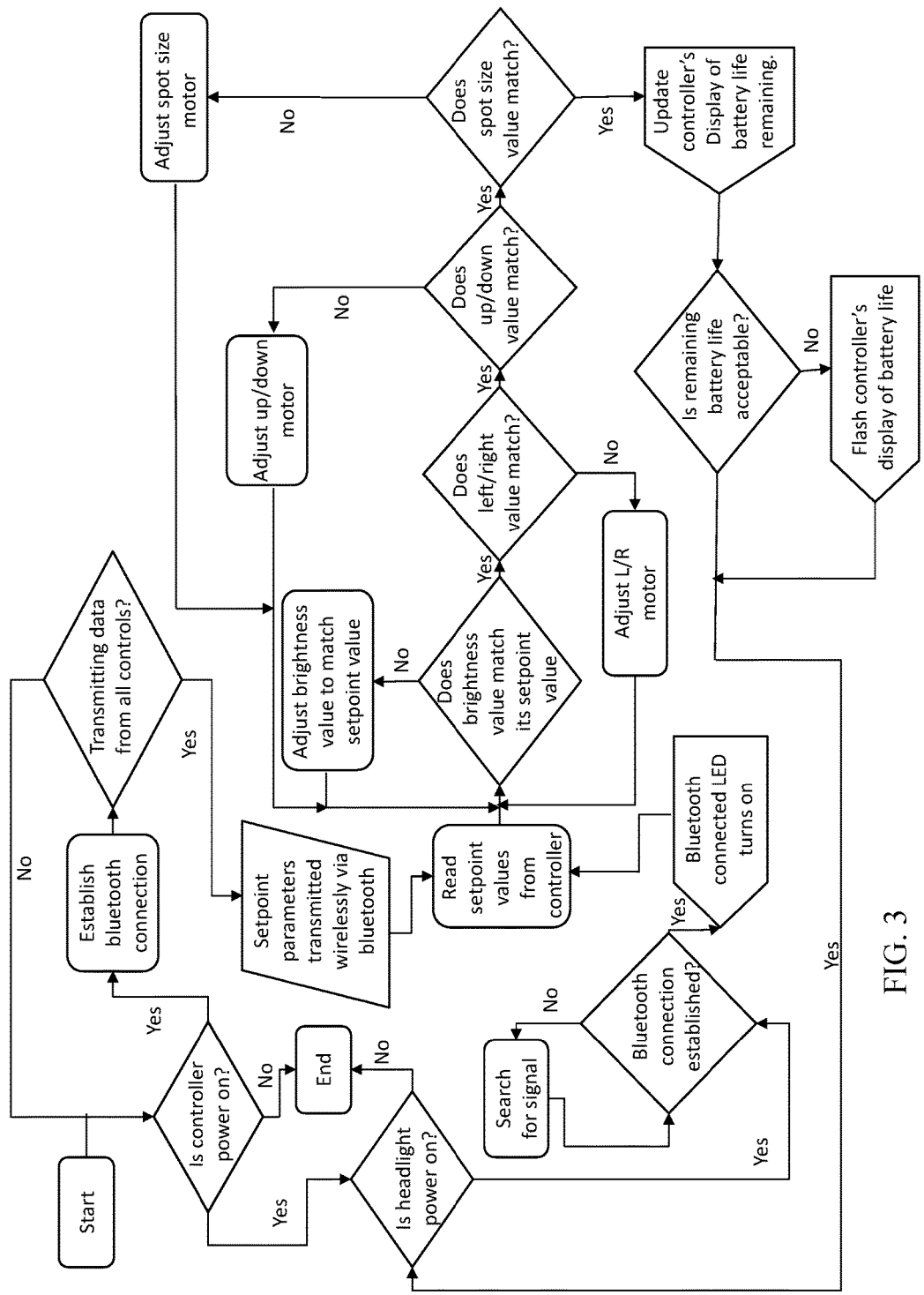
FIG. 3 is a functional flow diagram illustrating wireless connection and control between a wireless controller and a surgical headlight in accordance with various embodiments.

Referring now to FIG. 3, a method of controlling and operating the wireless surgical headlight 100 using the wireless controller 500 is provided in accordance with various embodiments. Although shown in FIG. 3 as using a Bluetooth® connection, it will be apparent in view of this disclosure that any other suitable electronic communications means can be used including, for example, near field communication (NFC), Bluetooth ®, wifi, cellular networks, any other suitable wireless communications, or combinations thereof.

In operation, max-to-min voltage data from the wireless controller is then converted into max-to-min position data for the first (left/right) and second (up/down) motors 201, 203. Encoder feedback data from the motors 201, 203 provides a reference for the processor 109 to evaluate. If-then-else type statements in software code of the processor 109 will decide the appropriate speed, direction, and distance to drive said motors until the conditions are met which satisfy input voltages from the controller's last transmission. The third (spot size) motor 205 may not require an encoder and feedback loop. In particular, the aperture can generally be over-driven utilizing a friction-drive such as an o-ring belt (e.g., 307*a*, 307*b*, 307*c*, and 307*d*). This arrangement simplifies the motor control as simply forward/reverse, and only requires the user to recognize the max/min condition and release the control.

In some embodiments, the program can loop, so that the motor 201, 203, 205 positions are constantly adjusted and updated continuously unless an event causes the control to exit the loop. Events causing the program loop to terminate or exit can include, for example, the user turning off the power source, low battery power, no user input is provided, the wireless communication link is broken between the controller 500 and the surgical headlight 100.

In some embodiments a power saver mode can be provided so that battery power may be conserved if transmitting data becomes unnecessary due to lack of user input. If the controller remains untouched for a prescribed period of time, a low-power mode of the controller 500 may transmit only as minimally necessary to maintain a wireless link with the paired headlight 100. Furthermore, in some embodiments, the motors 201, 203, 205 can be provided with a sufficient gear-reduction-ratio to prevent any movement of the light assembly 300 if power is temporarily removed. Thus, the surgical headlight can also enter a low-power mode, thereby further reducing power consumption.

While the present disclosure has been described with reference to certain embodiments thereof, it should be understood by those skilled in the art that various changes may be made and equivalents may be substituted without departing from the true spirit and scope of the disclosure. In addition, many modifications may be made to adapt to a particular situation, indication, material and composition of matter, process step or steps, without departing from the spirit and scope of the present disclosure. All such modifications are intended to be within the scope of the claims appended hereto.

What is claimed is:

1. A surgical headlight system comprising:
   a light assembly including:
      a light source having variable light output, and
      an optical assembly including an adjustable diameter aperture in optical communication with the light source;
   a motor assembly mounted to the light assembly including:
      a first motor configured to adjust an orientation of the light assembly relative to a horizontal plane,
      a second motor configured to adjust an orientation of the light assembly relative to a vertical plane, and
      a third motor configured to adjust the diameter of the aperture; and
   a sterilizable wireless controller configured to one or more of actuate at least one of the first motor or second motor of the motor assembly to alter the orientation of the light assembly relative to at least one of the vertical plane or the horizontal plane, actuate the third motor of the motor assembly to adjust the diameter of the aperture, vary the light output of the light source, or combinations thereof.

2. The system of claim 1, wherein the wireless controller is sterilized by autoclave.

3. The system of claim 1, wherein, control of the light within the sterile field is maintained by insertion of the wireless controller into a sterile and radiotransparent receptacle.

4. The system of claim 1, wherein the wireless controller includes a controller power source.

5. The system of claim 1, further comprising a belt for a waist of a user, a power source mounted to the belt for delivering electrical power to at least one of the light assembly or the motor assembly.

6. The system of claim 1, wherein the wireless controller includes at least one joystick or linear potentiometer for receiving input from the user.

7. The system of claim 1, wherein the light source is a light-emitting diode (LED).

8. The system of claim 1, wherein the light assembly further comprises a fiber optic cable in optical communication with the optical assembly.

9. The system of claim 1, wherein the light assembly further comprises one or more condensing lenses and an objective lens in optical communication with the light source.

10. A surgical headlight system comprising:
   a light assembly including:
      a light source having variable light output, and
      an optical assembly including one or more condensing lenses and an objective lens in optical communication with the light source;
   a motor assembly mounted to the light assembly including:
      a first motor configured to adjust an orientation of the light assembly relative to a horizontal plane,
      a second motor configured to adjust an orientation of the light assembly relative to a vertical plane, and
      a third motor configured to adjust a spacing between the one or more condensing lenses and objective lens; and
   a sterilizable wireless controller configured to actuate at least one of the first motor or second motor of the motor assembly to alter the orientation of the light assembly relative to at least one of the vertical or horizontal planes, actuate the third motor of the motor assembly to adjust the spacing between the one or more condensing lenses and objective lens, vary the light output of the light source, or combinations thereof.

11. The system of claim 10, wherein the wireless controller is sterilized by autoclave.

12. The system of claim 10, wherein, control of the light within the sterile field is maintained by insertion of the wireless controller within a sterile, radiotransparent receptacle.

13. The system of claim 10, wherein the wireless controller includes a controller power source.

14. The system of claim 10, further comprising a belt for a waist of a user, a power source mounted to the belt for delivering electrical power to at least one of the light assembly or the motor assembly.

15. The system of claim 10, wherein the wireless controller includes at least one joystick or linear potentiometer for receiving input from the user.

16. The system of claim 10, wherein the light source is a light-emitting diode (LED).

17. The system of claim 10, wherein the light assembly further comprises a fiber optic cable in optical communication with the optical assembly.

18. The system of claim 10, wherein the light assembly further comprises an adjustable diameter aperture in optical communication with the light source.

19. A method for operating a surgical headlight comprising:
   illuminating a surgical site with a beam of light emitted from a light assembly of a surgical headlight worn by a user;
   transmitting, in response to receiving a user input at a sterilizable wireless controller, instructions from the wireless controller to the surgical headlight; and
   in response to receiving the instructions at the surgical headlight, one or more of:
      actuating at least one of a first motor or a second motor of a motor assembly mounted to the headband and operatively connected to the light assembly, to alter the orientation of the light assembly relative to at least one of a vertical plane or a horizontal planes,
      actuating a third motor of the motor assembly to adjust at least one of a diameter of an aperture of the light assembly or a spacing between one or more condensing lenses and an objective lens of the light assembly, or
      varying a light output of the light assembly.

20. The method of claim 19, further comprising providing the user input to the wireless controller from within a surgical sterile field.

* * * * *